US00PP17024P3

(12) United States Plant Patent
Danziger

(10) Patent No.: US PP17,024 P3
(45) Date of Patent: Aug. 22, 2006

(54) ***TORENIA* PLANT NAMED 'DANCATPUR'**

(50) Latin Name: ***Torenia* sp.**
Varietal Denomination: Dancatpur

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 25 days.

(21) Appl. No.: 10/929,435

(22) Filed: Aug. 31, 2004

(65) Prior Publication Data

US 2006/0048253 P1 Mar. 2, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new and distinct *Torenia* plant named 'Dancatpur' characterized bydelicate, funnel form flowers consisting of four petals in which the top petal is pale violet-blue, RHS 91C, and the lower and side petals are deep violet-blue, RHS 89A, with a yellow-green blotch in the center of the lower petal, RHS 154A; its bushy and cascading growth habit, its dense branching which gracefully cascades from hanging baskets; its early flowering response and year round blooming in a moderate climate; its suitability as an annual for hanging pots outdoors under partial shade; and its optimal growth at the moderate temperature range of 15–25° C.

2 Drawing Sheets

Latin name of the genus and species of the plant claimed: *Torenia* sp.
Variety denomination: 'Dancatpur'.

BACKGROUND OF THE INVENTION

The present invention relates to a new and distinct cultivar of *Torenia* plant, botanically known as *Torenia* sp. of the Scrophulariaceae family, hereinafter referred to by the cultivar name 'Dancatpur'.

The new cultivar originated from a cross made in a controlled breeding program in Moshav Mishmar Hashiva, Israel. The female parent is the *Torenia* cultivar 'Dantopkmn' (patented, U.S. Plant Pat. No. 11,512). The male parent is an unnamed, unpatented bush type *Torenia* cultivar. 'Dancatpur' was discovered and selected by the inventor, Gabriel Danziger, as a single flowering plant within the progeny of the stated cross in a controlled environment in Moshav Mishmar Hashiva, Israel.

Asexual reproduction of the new cultivar by soft tip cuttings was first performed in May, 2002 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'Dancatpur' which in combination distinguish this *Torenia* as a new and distinct cultivar:

1. Delicate, funnel form flowers consisting of four petals in which the top petal is pale violet-blue, RHS 91C, and the lower and side petals are deep violet-blue, RHS 89A, with a yellow-green blotch in the center of the lower petal, RHS 154A;

2. Bush, cascading growth, maintains compact rounded growth;
3. Densely branched plant, gracefully cascading from hanging baskets;
4. Early flowering and year round blooming in moderate climate;
5. Suitable as an annual for hanging pots outdoors under partial shade; and
6. Optimal growth at moderate temperature range of 15–25° C.

Plants of the new *Torenia* cultivar 'Dancatpur' differ from plants of the parental cultivar 'Dantopkmn' (patented) in the characteristics described in Table 1. Plants of the unnamed, male parental cultivar (unpatented) are no longer unavailable to provide a comparison to the new cultivar 'Dancatpur'.

TABLE 1

| Character | New Cultivar *Torenia* sp. 'Dancatpur' | Parental Cultivar *Torenia* sp. 'Dantopkmn' (patented) |
|---|---|---|
| Flower color | Upper petal pale violet-blue, side and lower petals deep violet-blue, with yellow-green blotch in the center of lower petal | Upper petal white, side petals violet, lower petal light violet with yellow lengthwise stripes, violet outer corolla tube |
| Flower size (cm) | Depth: 3 cm<br>Width: 2.8 cm | Depth: 3.0 cm<br>Width: 3.2 cm |
| Growth habit | Bush, cascading | Cascading, pinching needed |
| Flowering time | 8 weeks from planting | 8 weeks from planting |

Of the many commercial cultivars known to the inventor, the most similar in comparison to 'Dancatpur' is the *Torenia* sp. cultivar 'Violet Moon' (unpatented) in the characteristics described in Table 2.

TABLE 2

| Characteristic | *Torenia* sp. 'Dancatpur' | *Torenia* sp. 'Violet Moon' (unpatented) |
|---|---|---|
| Flower color | Upper petal pale violet-blue, side and lower petals deep violet-blue, with yellow-green blotch in the center of lower petal | Red-Purple |
| Flower size (cm) | Depth: 3 cm<br>Width: 2.8 cm | Depth: 2.5 cm<br>Width: 2.5 cm |
| Growth habit | Bush, cascading | Bush, cascading |
| Flowering time | 8 weeks from planting | 8 weeks from planting |

'Dancatpur' has not been observed under all possible environmental conditions. The phenotype of the new cultivar may vary significantly with variations in environment such as temperature, light intensity, and day length without any change in the genotype of the plant. The following observations, measurements and values describe the new cultivar as grown in Moshav Mishmar Hashiva, Israel under conditions, which closely approximate those generally used in commercial practice.

BRIEF DESCRIPTION OF THE DRAWINGS

The accompanying photographic drawings show typical flower and foliage characteristics of 'Dancatpur' with colors being as true as possible with illustrations of this type.

The first photograph shows a full flowering plant of 'Dancatpur' in its entirety in a hanging basket.

The second photograph shows a close-up of 'Dancatpur' flowers showing the pale violet-blue flowers with deep violet-blue blotches surrounding the corolla, and central lobe blotched yellow at the base.

DETAILED BOTANICAL DESCRIPTION

The following observations, measurements and values describe the new cultivar as grown in Moshav Mishmar Hashiva, Israel under conditions, which closely approximate those generally used in commercial practice. Optimally, 'Dancatpur' is used as a pot plant, grown outdoors in moderate climate, indoors during winter. Irrigation and fertilization is recommended on a regular basis. 'Dancatpur' is best grown in full sunlight; partial shade is required in mid summer. A fully grown 'Dancatpur' plant takes 3 months. 'Dancatpur' blooms year-round in moderate climate.

Color references are made to The Royal Horticultural Society Color Chart (R.H.S.), except where general colors of ordinary significance are used. Color values were taken under daylight conditions at approximately noon in Moshav Mishmar Hashiva, Israel.

The age of the plants described is 3 months. The 'Dancatpink' plants described were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'Dancatpink' were fertilized up to a level of 59 ppm N, 35.4 ppm P and 94.4 ppm K.

Propagation: Tissue culture and soft tip cuttings.

Plant:

*Form.*—Bush, cascading.

*Growth habit.*—Compact, rounded.

*Height.*—15 cm.

*Spread.*—50–60 cm.

*Blooming period.*—Year round in moderate climate.

*Cold tolerance.*—Plants may be damaged by temperatures below 12° C.

*Vigor.*—Fully grown plant in 3 month during summer.

Stem:

*Color.*—Green, RHS 143-A.

*Length.*—30 cm.

*Diameter.*—2 mm.

*Pubescence.*—Minimal.

*Branching.*—Between 5 and 10 main branches grow from the base and split into hundreds of secondary branches.

*Length of internodes.*—3–4 cm.

Foliage:

*Overall shape.*—Obovate.

*Base.*—Triangular, Cordate.

*Tip.*—Acuminate.

*Margin.*—Serrate.

*Color.*—Center color of leaf: Green, RHS 137-A. Upper side: Green, RHS 137-A. Under side: Yellow-Green, RHS 146-B.

*Size of leaf.*—Width: 3.5 cm. Length: 4.5 cm. Leaf Texture: Smooth, few hairs.

*Venation.*—Not prominent. Pattern: Anastomotic; midrib to 4–6 secondary veins. Color: Upper surface: Green, RHS 137A. Lower surface: Yellow Green, RHS 146B.

*Petioles.*—Length: 1 cm. Width: 1.5 mm. Color: Yellow-Green, RHS 146-B.

Flowers:

*Blooming period.*—Typical: Year round in moderate climate; Observed: February to November in Moshav Mishmar Hashiva, Israel.

*Time for plant to produce flowers.*—About 3 weeks from planting cutting in summer season.

*Quantity of flowers.*—Per lateral stem: About 4–6; Per plant: About 200–400.

*Flowering stem.*—Flowers appear along the growing stems.

*Flower longevity on the plant.*—About 9 months.

*Lastingness of the individual bloom* (*vase life*).—About 2–5 days.

*Fragrance.*—None.

*Orientation at opening.*—Slanted upward.

*Type.*—Single.

*Shape.*—Overall: Funnel-form; 5-winged; Corolla tube: cylindrical or often broadened above; Corolla: 2-lipped, the upper lip faintly 2-lobed, the lower lip 3 lobed.

*Flower size.*—Depth: About 3 cm. Width: About 2.8 cm.

*Petals.*—Number: Four and fused. Petal size: Length: Upper: About 2.5 cm; Sides: About 1.8 cm; Lower: About 1.7 cm. Width: Upper: About 1.6 cm; Sides: About 0.7 cm; Lower: About 1.3 cm. Shape: Upper: Overall: orbicular, Apex: rounded, Base: fused; Sides: Overall: spatulate, Apex: rounded, Base: fused; Lower: Overall: spatulate, Apex: rounded, Base: fused. Margin: Entire and undulated and picotee. Color: The upper lip pale violet-blue, lower and side lips deep violet-blue, with yellow-green blotch in the center of lower lip. Mature: Upper side: Upper lip: pale violet-blue, RHS 91C; Lower and side lips: deep violet-blue, RHS 89A, with a yellow-green blotch in the middle of the lower lip, RHS 154A.

Under side: Upper lip: pale violet-blue, RHS 91B; Lower and side lips:, deep violet-blue, RHS 89B, with a yellow-green blotch in the middle of the lower lip, RHS 150C. Margin: Upper side: Deep violet-blue, RHS N89A; Under side: Violet, RHS 88A. Throat: Pale violet-blue, RHS 91C, yellow-green, RHS 154A color changes going down the throat. Immature: Upper side: Upper lip: Primarily violet-blue RHS 91C, with deep violet-blue color in middle, RHS N89A; Lower lip: Primarily violet, RHS N88A, with violet-blue, RHS 91C near base. Side lips: Deep violet-blue, RHS N89A, with a yellow, RHS 4A, blotch in the middle of the lower lip. Under side: Upper lip: Primarily violet-blue, RHS 91A, with violet color in middle, RHS N88A; Lower and side lips:, Primarily violet, RHS N88A, with violet-blue, RHS 91B near base, with a yellow-white, RHS 158A blotch in the middle of the lower lip. Margin: Violet, RHS N88A (same for upper and under side of immature petals). Throat: Violet-blue, RHS 91B, to yellow-orange, RHS 14B, color changes going down the throat.

*Floral tube.*—Length: Typical: About 3 cm; Observed: About 3 cm. Width: Typical: About 3 cm; Observed: About 3 cm. Color: Yellow-Green, RHS 154B, and Violet-Blue, RHS 91B (on the outside and on the inside).

*Sepals.*—Number: 5. Length: About 2 cm. Width: About 0.5 cm. Shape: Two-lobed, 5 winged. Apex: Acute. Base: Wedge shaped. Margin: Undulated. Color: Yellow-green, RHS 144A.

*Peduncle.*—Length: 2 cm. Diameter: About 0.2. Color: Green, RHS 143-B. Texture: Few hairs on edges of the peduncle.

*Bud.*—Shape: Oblong, cylindrical, ellipsoid, 5 winged. Size: Length: About 25 mm. Diameter: About 10 mm. Color: Deep violet-blue, RHS 89A, to pale violet-blue, RHS 91C, to green, RHS 143B (apex to base). Texture: Pubescence on winged edges.

Reproductive organs:

*Androecium.*—Stamen: Number: 2 pairs per flower, fused. Color: Violet-Blue, RHS 92 D. Anther: Length: About 0.4 cm; upper anthers shorter — about 0.3 cm. Width: About 1 mm. Color: Violet-Blue, RHS 92 B. Spur: Present.

*Filament.*—Length: About 1.3 cm; lower filaments shorter — about 0.5 cm. Width: About 5 mm. Color: Violet-Blue, RHS 92 D.

*Pollen.*—Amount: Sparse. Color: White, RHS N155B. Requirements: Young flowers, vital pollen, and receptive, open stigma.

*Gynoecium.*—Pistil: Number: One per flower. Length: About 2.4 cm. Stigma: Shape: Two lobes, open to opposite side, deltoid shape. Length: About 0.2 cm. Width: About 0.2 cm. Color: Violet-Blue, RHS 92D. Style: Length: About 1.8 cm. Color: Violet-Blue, RHS 92 D. Ovary: Number: 1. Length: About 0.6 cm. Width: About 2 mm. Color: Green, RHS 143-B.

Seed/fruit: None.

Pest/disease resistance and/or susceptibility: Susceptible to Powdery Mildew.

I claim:

1. A new and distinct *Torenia* plant named 'Dancatpur', as illustrated and described herein.

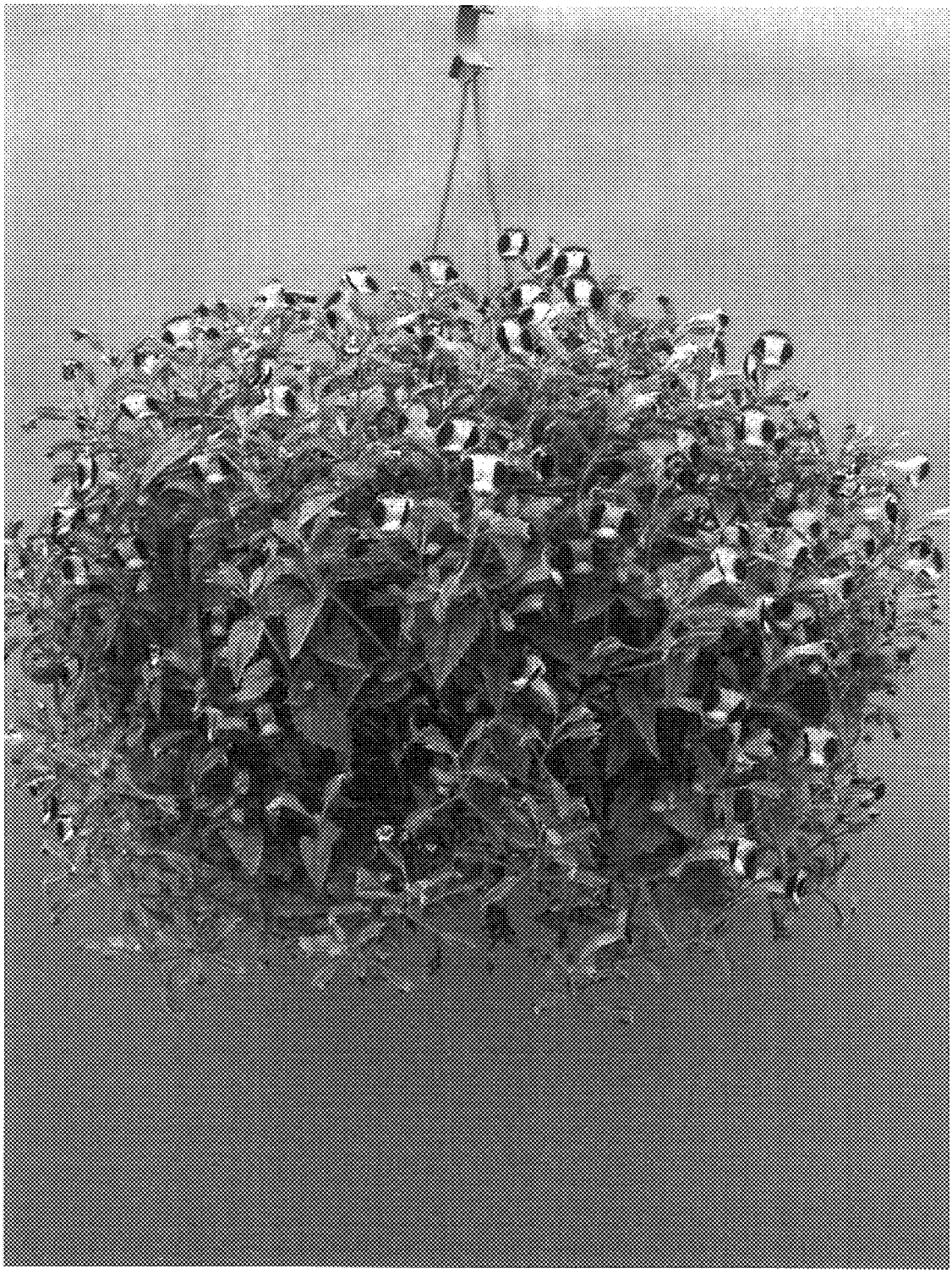

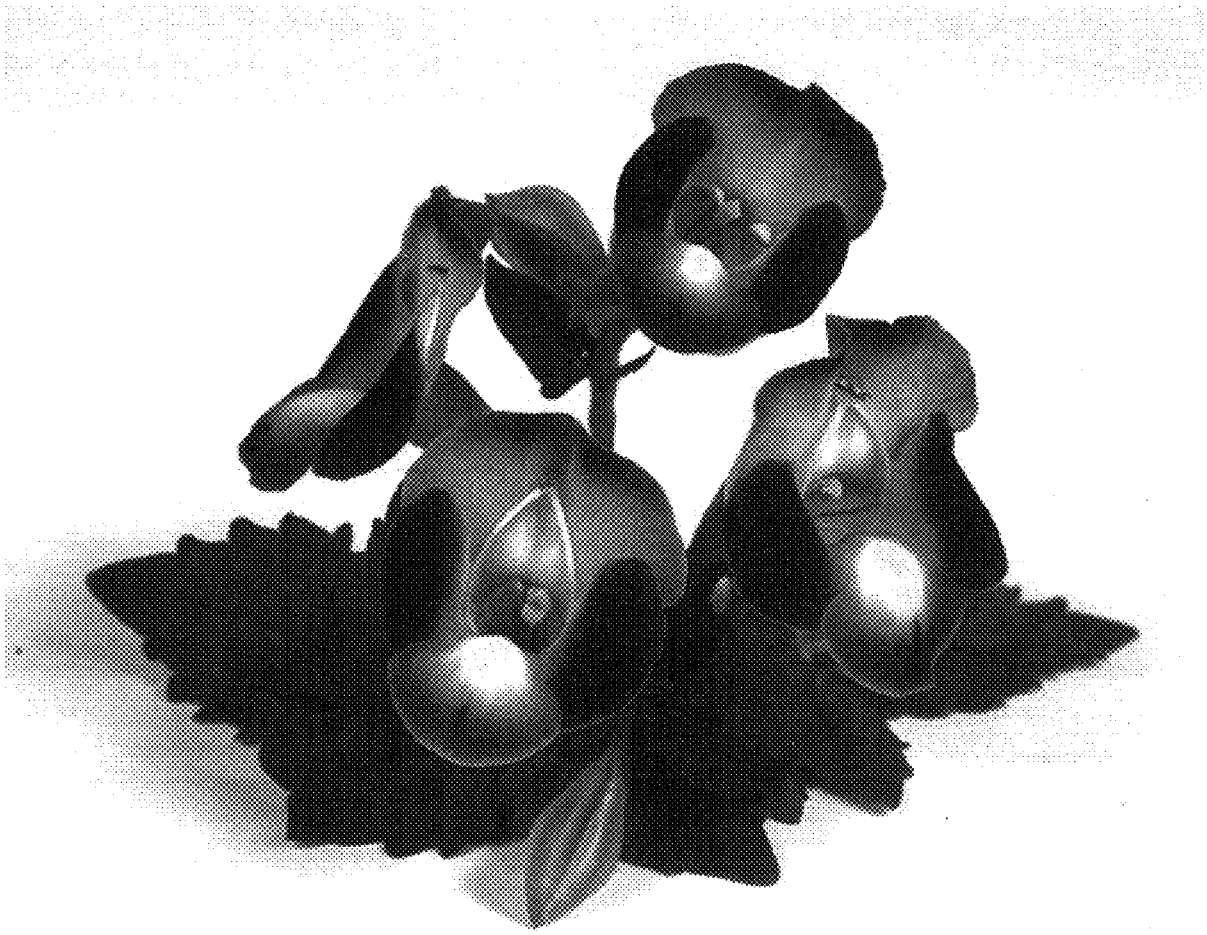

* * * * *